United States Patent [19]

Nieters et al.

[11] Patent Number: 5,631,424

[45] Date of Patent: May 20, 1997

[54] METHOD FOR ULTRASONIC EVALUATION OF MATERIALS USING TIME OF FLIGHT MEASUREMENTS

[75] Inventors: Edward J. Nieters, Rexford; Robert S. Gilmore, Burnt Hills; Michael F. X. Gigliotti, Jr., Scotia, all of N.Y.

[73] Assignee: General Electric Company, Schenectady, N.Y.

[21] Appl. No.: 509,679

[22] Filed: Jul. 31, 1995

[51] Int. Cl.[6] .................................................. G01N 29/04
[52] U.S. Cl. .................................... 73/598; 73/588
[58] Field of Search ........................... 73/597, 598, 599, 73/600, 602, 588

[56] References Cited

U.S. PATENT DOCUMENTS

| 4,100,808 | 7/1978 | Evans et al. | 73/588 |
|---|---|---|---|
| 4,173,139 | 11/1979 | Conn | 73/1 DV |
| 4,184,373 | 1/1980 | Evans et al. | 73/588 |
| 4,215,583 | 8/1980 | Botsco et al. | 73/582 |
| 4,366,713 | 1/1983 | Gilmore et al. | 73/618 |
| 4,479,386 | 10/1984 | Beggs et al. | 73/582 |
| 4,893,510 | 1/1990 | Ichikawa et al. | 73/620 |
| 5,038,787 | 8/1991 | Antich et al. | 73/602 |
| 5,046,363 | 9/1991 | Moore | 73/588 |
| 5,197,475 | 3/1993 | Antich et al. | 73/602 |
| 5,303,590 | 4/1994 | Modderman et al. | 73/588 |
| 5,383,366 | 1/1995 | Wallingford | 73/602 |
| 5,408,882 | 4/1995 | McKinley et al. | 73/597 |

*Primary Examiner*—Hezron E. Williams
*Assistant Examiner*—Richard A. Moller
*Attorney, Agent, or Firm*—Douglas E. Erickson; Marvin Snyder

[57] ABSTRACT

A nondestructive evaluation method is described for ultrasonic evaluation and detection of features in polycrystalline materials, such as grain orientation (e.g. texturing) or grain boundary orientation. The method may, for example, be employed to detect diffusion bonds that contain undesirable planar grain boundary arrays. The method utilizes time of flight statistics gathered from reflections associated with incident ultrasonic signals directed into a plurality of locations within the material.

19 Claims, 15 Drawing Sheets min (0V)  max (10V)

3.0 µs                                    6.0 µs

METHOD FOR ULTRASONIC EVALUATION OF MATERIALS USING TIME OF FLIGHT MEASUREMENTS

This invention is subject to certain rights of the U.S. Government under the terms of contract FAA-93-608-029.

FIELD OF THE INVENTION

This invention relates generally to a nondestructive method of evaluating a polycrystalline material using ultrasound for the purpose of detecting certain microstructural features within the material. More particularly, it is a method wherein the time of flight of a plurality of reflected ultrasonic pulses at a plurality locations can be used to identify microstructural features such as planar grain boundary fronts, grain texturing and differential grain sizes. In one specific embodiment, it is a method for evaluating the interfaces between bonded materials, such as diffusion bond interfaces.

BACKGROUND OF THE INVENTION

Nondestructive evaluation techniques have been developed that can identify diffusion bonds that contain chemical contamination of the bonding interfaces, or arrays of pores resulting from incomplete bonding. U.S. Pat. No. 4,173,139 describes calibration standards for ultrasonic flaw detection of diffusion bonds that contain voids. U.S. Pat. No. 4,215,583 describes an apparatus and associated method of identifying disbonded regions in diffusion bonds by the reflection of sound from such flaws. It is known that disbonds can be imaged by techniques such as acoustic microscopy, that employ high frequency (140 MHz) sound energy. Lower frequency ultrasonic energy, such as that used in well-known C-scan evaluation techniques, may also be used to detect voids, and the reflection data from bonds containing voids has been related to the tensile strength of the bonds.

It has been observed that even when diffusion bonds are formed that do not contain voids or chemical contamination when evaluated using various ultrasonic and other known materials evaluation techniques, including destructive techniques such as optical and SEM metallography, that it is possible to have bonds that have significantly reduced, or non-optimum, mechanical properties, such as tensile and shear strength, than the adjacent materials between which the bond is formed. This difference in mechanical properties appears to be largely related to the dgree to which diffusion processes have prompted grain growth across the interface. If the grains are aligned along the interface, such as in the form of a planar array, the mechanical properties are generally reduced. If grain growth has occurred across the interface, the mechanical properties are generally improved. While useful for the evaluation of voids and chemical contamination at bonded interfaces, known ultrasonic techniques, such as C-scan evaluation, do not positively identify bonded interfaces that are non-optimum, as described further.

Because of the desirability of using ultrasonic nondestructive evaluation (NDE) techniques to detect microstructural features, such as non-optimum bond interfaces as described herein, it is therefore desirable to develop ultrasonic detection and evaluation methods that are capable of identifying these features.

SUMMARY OF THE INVENTION

Microstructural features in polycrystalline materials, such as grain orientation (e.g. texturing), grain boundary orientation (e.g. planar grain boundary arrays) or grain size differentials (e.g. differentials due to critical grain growth in Ni-base superalloys where the differential in grain size may be two to three orders of magnitude, may be detected and evaluated using time of flight information gathered from reflections associated with incident ultrasonic signals directed into a plurality of locations within the materials. This method may be used, for example, to detect and evaluate diffusion bonds in materials that contain unacceptable planar grain boundary arrays.

The invention may be briefly described as a method of detecting and evaluating microstructural features comprising regions of grain orientation or crystallographic texture, grain boundary orientation or grain size differential within a volume of a material having a microstructure comprising a plurality of randomly oriented grains defining a randomly oriented network of grain boundaries, comprising the steps of: insonification of a plurality of locations within the volume of the material by using a transducing means to send an ultrasonic pulse through each location, whereby the ultrasonic pulse produces at each location a plurality of reflections characteristic of the microstructure of the material at that location, each reflection having a characteristic amplitude and time of flight; detection of the amplitude and the time of flight for each of the plurality of reflections at each location; identification of a time of flight ($TOF_M$) value of the reflection at each location having the largest amplitude; storing information comprising the $TOF_M$ value at each location and the associated location in an information storage means; and comparing the value of $TOF_M$ at one location with the values of $TOF_M$ at a plurality of other locations for the purpose of determining whether a region of adjacent locations exist having the same $TOF_M$, whereby a region of adjacent locations having the same values of $TOF_M$ are indicative of grain orientation or grain boundary orientation within the material.

This time of flight information may be converted into a number of useful forms that may be used to characterize certain features of these polycrystalline materials, such as for example, histograms that integrate the time of flight information for a particular set of locations within a material, as well as two-dimensional and three-dimensional plots that illustrate time of flight as a function of a plurality of locations within a given material. The locations analyzed may be selected so as to evaluate time of flight reflectance conditions at a known location or locations within a material, or the method may be used to detect unknown microstructural features by detecting certain time of flight reflectance characteristics from such features, or a combination of these methodologies may be utilized.

DETAILED DESCRIPTION OF THE INVENTION

Figure 1A:
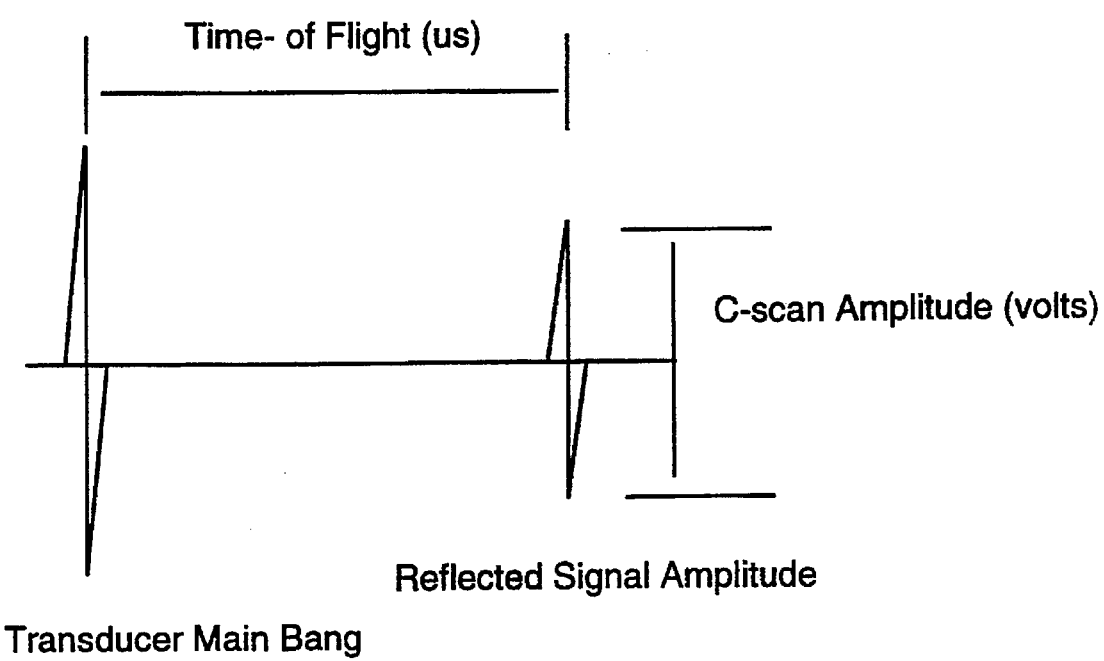
FIG. 1A illustrates the difference between C-scan and time-of-flight measurements for a given incident ultrasonic pulse and reflection.

Ultrasonic time-of-flight measurement from an inspected volume is a well-known NDE procedure by which an incident ultrasonic pulse is introduced into a material under evaluation. The incident ultrasonic pulse is known to interact with certain features within the material, such as voids or regions having a different chemical composition, so as to produce a reflected signal. The time of flight is the interval of time that elapses between initiation of the incident pulse and the reception of the reflected signal, as illustrated schematically in FIG. 1A. The time of flight corresponds to interactions with features from a volume (depth region) at a particular location within the object. Time of flight measurements are currently used primarily in conjunction with amplitude information (as also shown in FIG. 1A) to characterize features within that volume as, for example, is the case with C-scan imaging and data analysis techniques that have been used to detect voids and chemical composition changes in various materials. Using C-scan techniques, the amplitude of the reflected signal is used to detect and evaluate a feature, and the time of flight of the reflected signal is sometimes used to determine the depth of the feature. Time of flight measurements have not been used to image microstructural features directly. However, Applicants have determined that the time of flight of reflected ultrasonic pulses can be used to detect and evaluate certain microstructural features, comprising regions of grain orientation or crystallographic texture, grain boundary orientation or grain size differential within a volume of a material having a microstructure comprising a plurality of randomly oriented grains defining a randomly oriented network of grain boundaries, and herein describe a method for accomplishing such detection and evaluation, including the imaging of such features.

This invention may be generally described as a method of detecting and evaluating microstructural features comprising regions of grain orientation or crystallographic texture, grain boundary orientation or grain size differential within a volume of a material having a microstructure comprising a plurality of randomly oriented grains defining a randomly oriented network of grain boundaries, comprising the steps of: insonification of a plurality of locations within the volume of the material by using a transducing means to send an ultrasonic pulse through each location, whereby the ultrasonic pulse produces at each location a plurality of reflections characteristic of the microstructure of the material at that location, each reflection having a characteristic amplitude and time of flight; detection of the amplitude and the time of flight for each of the plurality of reflections at each location; identification of a time of flight ($TOF_M$) value of the reflection at each location having the largest amplitude; storing information comprising the $TOF_M$ value at each location and the associated location in an information storage means; and comparing the value of $TOF_M$ at one location with the values of $TOF_M$ at a plurality of other locations for the purpose of determining whether a region of adjacent locations exist having the same $TOF_M$, whereby a region of adjacent locations having the same values of $TOF_M$ are indicative of grain orientation or grain boundary orientation within the material.

It is preferred that this method be utilized to detect and evaluate microstructural features comprising regions of grain orientation or crystallographic texture, grain boundary orientation or grain size differential within a volume of a material having a microstructure comprising a plurality of randomly oriented grains defining a randomly oriented network of grain boundaries, however, other applications of the method are possible where a differential in the time of flight of the reflected signal in a material occurs.

Figure 1B:
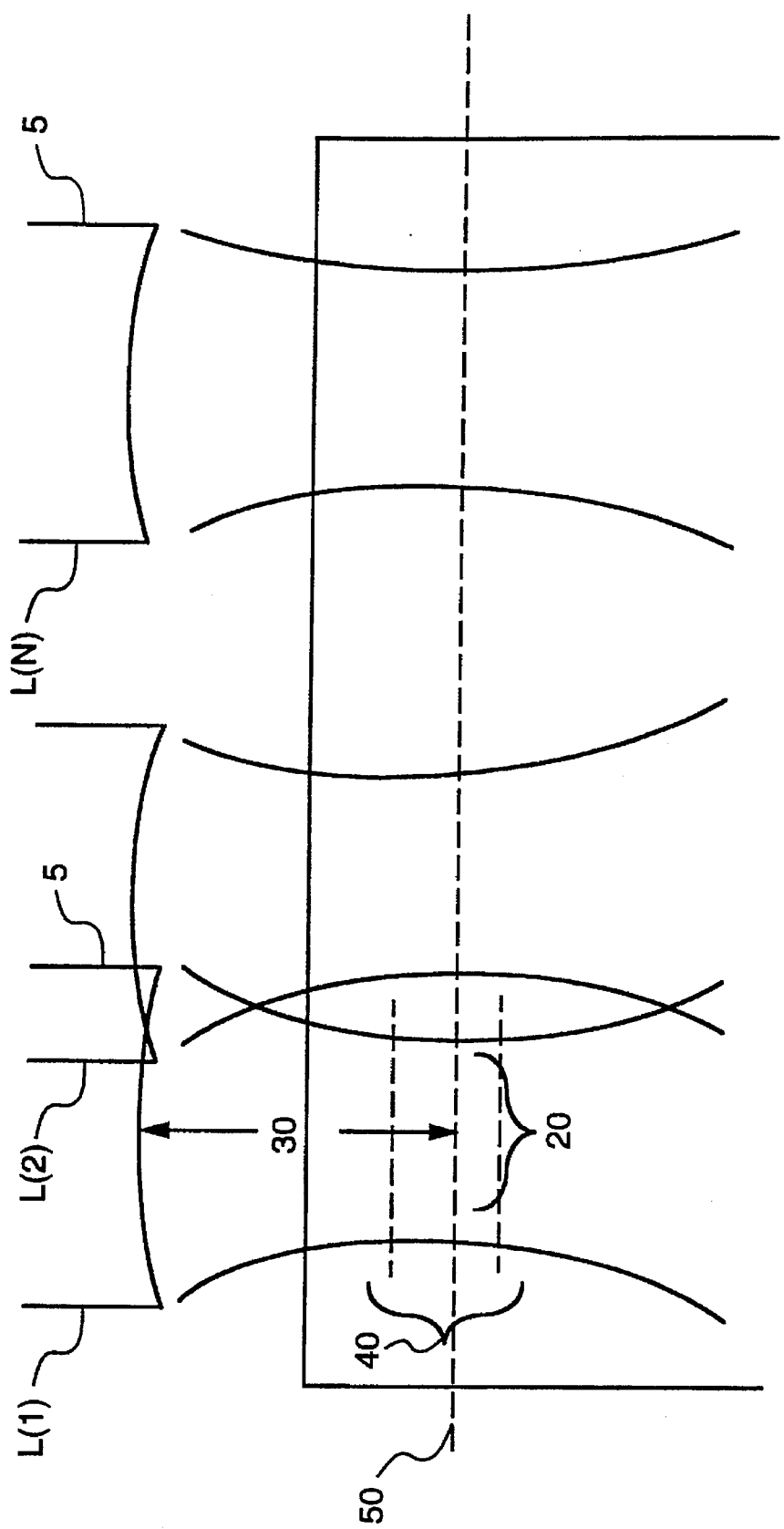
FIG. 1B illustrates the use of such a transducer in the method of this invention.
Figure 1C:
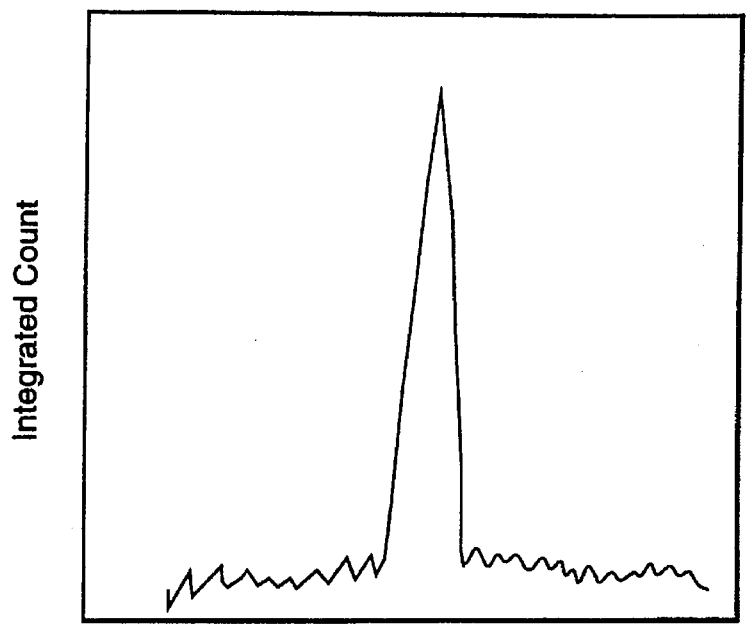
FIG. 1C is an illustration of one possible result of the integration of the $TOF_M$ information from a plurality of locations (normal incidence).
Figure 1D:
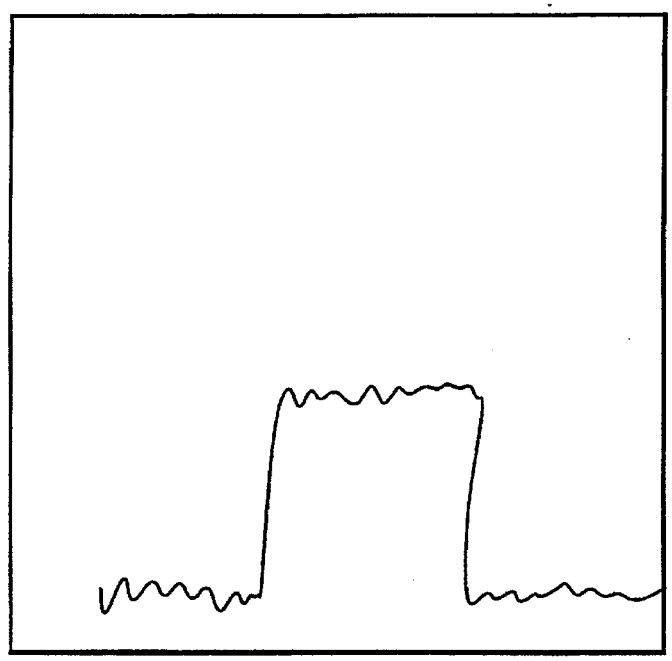
FIG. 1D is an illustration of one possible result of the integration of the $TOF_M$ information from a plurality of locations (non-normal incidence).

The first step comprises insonification of a plurality of locations within the volume of the material by using a transducing means to send an ultrasonic pulse through each location, whereby the ultrasonic pulse produces at each location a plurality of reflections characteristic of the microstructure of the material at that location, each reflection having a characteristic amplitude and time of flight. Insonification may be done using any suitable transducing means capable of generating an ultrasonic pulse (typically in the range of 0.5–100 Mhz), such as piezoelectric transducing means of a type well-known in the art. The tranducing means may comprise a contact or immersion type transducer. The transducing means may also comprise an array or a single element transducer. Among single element transducing means, the transducer may be either focused or unfocused. However, it is preferred for applications such as the analysis of diffusion bonds, to use a single element, focused immersion type transducer of a type well-known for use in C-scan analysis, and commercially available. Fig. 1B illustrates the use of such a transducer in the method of this invention. A focused pulse from a transducer 5 of circular cross-section produces an ultrasonic pulse 10 that focuses to an area of diameter 20, at a depth 30, and having a depth of field 40 that may be calculated from known characteristics of the transducer, immersion medium and material to be insonified. In a polycrystalline material comprising a plurality of randomly oriented grains and grain boundaries, the pulse will be randomly reflected by the grain boundaries, resulting in a series of random times of flight from within the inspected volume at that location (L1). However, if there exists, for example, within the inspected volume (roughly defined by the volume within the depth of field at the particular location of interest) a region 50 of oriented grain boundaries, the resulting times of flight from region 50 will (assuming that the region is nearly perpendicular to the incident pulse) be the same, or substantially similar due to the fact that these boundaries do not form a flat plane, but rather approximate a plane resulting in minor variations in the time of flight of the pulse from different points within the region. This phenomena will result in a reflection having an amplitude that is greater than that of the other reflections within the inspected volume, and an associated time of flight (referred to herein as $TOF_M$) at location L1. By integrating the $TOF_M$ results from a plurality of locations (L(1), L(2), L(3) . . . L(N), the reflections from a region 50 having the same, or a substantially similar, time of flight will produce a characteristic peak that may be used to identify region 50, as illustrated in FIG. 1C. This $TOF_M$ and location information may also be plotted either two-dimensionally or three-dimensionally to develop images of region 50. Other microstructural features such as grain orientation or crystallographic texturing, or certain grain size differentials may also be detected and evaluated by this method, because these features will also effect the measured time of flight at the locations within the microstructure where a transition takes place, and the resulting times of flight of reflections from an incident ultrasonic pulse within a given volume are non-random. Returning to the example of grain boundary orientation, if a region 60 exists that is not normal to the incident pulse, but is oriented at an angle to the pulse such that it is capable of reflecting the pulse to the transducing means, it is expected that the integrated data will still exhibit a peak, although the peak would be flattened corresponding to the distribution in the times of flight, as illustrated in FIG. 1D. Also, time of flight can easily be translated into an indication of depth of a detected microstructural feature so long as the speed of sound in the material being evaluated is known.

The step of detection of the amplitude and the time of flight for each of the plurality of reflections at each location may be done using known detection means and methods, as used for example in C-scan analysis. It is preferred that the step of detection be done using the same transducing means that is used to initiate the incident ultrasonic pulse. However, it is also possible to use a different detection means to detect the reflected ultrasonic signal. Such detection means may include a single transducer, or a plurality of transducers, and need not be the same type of transducer utilized to generate the incident ultrasonic pulse. For example, for microstructural features that may reflect at angles such that they may not be detected by the transducing means used to generate the incident ultrasonic pulse, it may be desirable to use a separate detection means positioned to receive the reflected signal.

The step of identification of a time of flight ($TOF_M$) value of the reflection at each location having the largest amplitude may be done using any suitable means. For example the detected reflected waveform signals from a particular location may be captured in a type of well-known circular buffer wherein as the signals are received, each new maximum value is stored to the exclusion of any previously stored (lesser) values. Thus, as the entire reflected waveform from each location is passed through the buffer, only the largest amplitude, and associated $TOF_M$ is retained. This useful to minimize the amount of data that must be stored for each location, however, this step could also comprise storing all, or some portion, of the reflected waveform so long as it includes and identifies $TOF_M$.

The step of storing information comprising the $TOF_M$ value at each location and the associated location in an information storage means may be accomplished using any suitable means, including analog or digital information storage means, including temporary or permanent storage means, such as a data acquisition computer. It is preferred to use information storage means that are similar to those used to store C-scan information.

The step of comparing the value of $TOF_M$ at one location with the values of $TOF_M$ at a plurality of other locations for the purpose of determining whether a region of adjacent locations exist having the same, or a substantially, $TOF_M$, whereby a region of adjacent locations having the same values of $TOF_M$ are indicative of non-random microstructural features, such as regions of grain orientation or crystallographic texture, grain boundary orientation or grain size differential within a volume of a material, may be done using any suitable methods or means. This may include histograms of $TOF_M$ for a plurality of locations, or two-dimensional or three-dimensional plots of $TOF_M$ as a function of location, as described further herein, or other comparisons. Comparing could also include an automated system that compared, for example, numerical data such as the data that would be utilized to generate a histogram as described herein, without displaying this information to a human user, such that the system would automatically make a determination as to the presence or absence a particular microstructural feature.

Among many potential applications, the method of this invention may be applied to the inspection of many types of bonds. Particularly, those types of bonds where the processing of the bonds can result in significant variations in their mechanical properties, due to microstructural changes at the bond interface, such as changes that have been observed to occur in the case of diffusion bonds. In diffusion bonding generally, two or more materials are placed in pressing contact, often under some for of an applied load, and heat is applied at a temperature sufficient to cause diffusion across the interface between the materials. Where the time, temperature or pressure are insufficient, diffusion bonding is incomplete and voids are known to exist at the interface. Such voids may be detected non-destructively using C-scan analysis techniques. It is also possible to have a diffusion bond where all pores, voids, and cracks have closed, such that C-scan analysis does not detect any undesirable microstructural features, and yet the bond interface is may be planar. A planar interface is indicative of the fact that diffusion has not yet progressed across the interface. Diffusion bonds in this condition have been observed to have non-optimum mechanical properties, as the bond interface represents a path of least resistance for crack propagation. Thus it is more desirable to allow bonding to proceed until diffusion processes have progressed to the point that grain growth proceeds across the bond interface, as described further herein. C-scan analysis does not provide a suitable means for non-destructively evaluating such microstructural changes, however, as described herein, time of flight analysis may be used to non-destructively determine when diffusion has progressed across the interface, because upon a sufficient degree of diffusion, the grain boundaries are no longer ordered along the interface. Thus, the time of flight signal would change from showing a peak at the interface (in the case of insufficient diffusion) to showing no peak once diffusion has progressed across the interface, and the microstructure in the region of the interface has resulted in a random orientation of grain boundaries. With respect to bonding applications, this invention may be described as a method of evaluating an article formed by bonding together a plurality of materials, each material having a microstructure comprising a plurality of randomly oriented grains defining a randomly oriented network of grain boundaries, and containing an internal interface where the materials are bonded to one another, comprising the steps of: insonification of a plurality of locations within the article, including locations that comprise the internal interface, by using a transducing means to send an ultrasonic pulse through each location, whereby the ultrasonic pulse produces at each location a plurality of reflections characteristic of the microstructure of the materials at that location, each reflection having a characteristic amplitude and time of flight; detection of the amplitude and the time of flight for each of the plurality of reflections at each location; identification of a time of flight ($TOF_M$) value of the reflection at each location having the largest amplitude; storing information comprising the $TOF_M$ value at each location and the associated location in an information storage means; and comparing the value of $TOF_M$ at one location with the values of $TOF_M$ at a plurality of other locations for the purpose of determining whether a region of adjacent locations exist having the same $TOF_M$, whereby a region of adjacent locations at the internal interface having the same values of $TOF_M$ are indicative of incomplete bonding between the materials.

The method of this invention can also be combined with well-known C-scan analysis methods to provide a more comprehensive method of detection and evaluation of the microstructural characteristics of various types of materials, particularly since the techniques are so compatible with and complementary to one another. These methods are compatible in that the same apparatus may be used to generate the incident ultrasonic pulses and receive the reflected signal. It is only necessary to modify a C-scan analysis apparatus so as to also collect and evaluate the time of flight information as described herein. Once collected and evaluated, C-scan and time of flight information may utilized separately, or in combination with one another, to detect and evaluate certain microstructual features of an article. They are complementary in that each method may be utilized to detect those features for which it is best suited. For example, in evaluating an article containing a diffusion bond, C-scan analysis can be used to detect the presence of voids or contamination at the bond interface, while time of flight information may be used to determine whether the diffusion bond interface contains undesirable grain boundary alignment, or whether a desirable diffusion bond has been formed.

EXAMPLE 1

The method of this invention was utilized to evaluate diffusion bonds in samples that were bonded under different conditions. A diffusion bond of high strength requires an absence of voids, pores and cracks; it also requires that the grain boundaries at the bond line interface be similar to the surrounding parent material grain structure, i.e., random and non-planar. Non-random, planar orientation of the grains decreases the bond's strength and quality.

Time-of-flight imaging, the NDE method of this invention, records the point in time ($TOF_M$) where a given (maximum) C-scan amplitude occurs. FIG. 1A shows the difference between C-scan and time-of-flight measurements for a given ultrasonic trace.

It is possible to have a diffusion bond where all pores, voids, and cracks have closed, and yet the bond interface is planar. In this example, titanium alloy blocks were bonded under three conditions, all conditions yielding a bond line substantially free of voids, pores, and cracks. However, only one process condition yields a bond region free of a planar grain boundary array.

Rectangular blocks of a titanium alloy commonly referred to as "Ti-17" (Ti-5 Al-2 Sn-2 Zr-4 Cr-4 Mo, in weight percent) were prepared with a cross-section of 2.1"×2.6" (5.3 cm×6.6 cm) and in thicknesses of 1" (2.5 cm) or 0.5" (1.3 cm). Three blocks were assembled for diffusion bonding of a 1" and 0.5" thick piece together with their common cross-sections aligned by clamping the mating surfaces together and electron beam (eb) welding the perimeter edge of the bonding planes together in a vacuum. The blocks were hot isostatically pressed at three conditions: Block 17H1 was processed with 15,000 psi (103 MPa) applied pressure at 865° C., 2 hours, and 800° C., 4 hours. Block 17H2 was processed with 15,000 psi (103 MPa) applied pressure at 910° C., 2 hours, and 800° C., 4 hours. Block 17H3 was processed with 15,000 psi (103 MPa) applied pressure at 800° C., 4 hours.

Figures 2A, 2B, 2C:
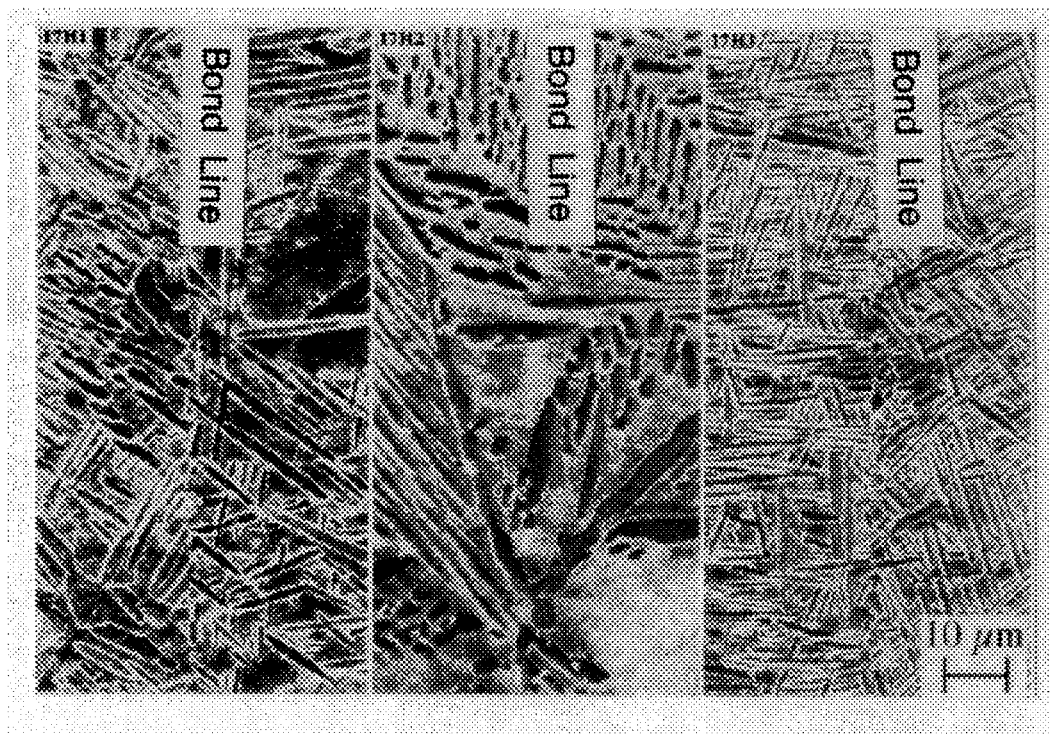
FIGS. 2A–C scanning electron micrographs of three Ti-base alloy blocks containing diffusion bonds that were processed under different diffusion bonding conditions.

These diffusion bonds were examined by light and scanning electron microscopy, revealing that the bond lines of all three samples were free of voids, pores, and cracks. Scanning electron micrographs of the three bonded blocks 17H1, 17H2 and 17H3 are displayed in FIGS. 2A–C., respectively. With reference to FIGS. 2A and 2C, all bonds are void-, pore- and crack- free, however, samples 17H1 and 17H3 exhibit a planar array of grain boundaries along the original diffusion bond interface, while sample 17H2 does not. The method of this invention was then utilized to detect the presence or absence of planar bond arrays using these samples. Because of the asymmetry of the bond interface (1" from one end and 0.5" from the other end of the sample), a single focused, immersion transducer could be used to scan a plurality of locations within the volume of a given sample both in the alloy matrix and at the diffusion bond interface, simply by inverting the sample. Thus, it was possible to determine the effectiveness of the technique for evaluating microstructural variations, such as grain boundary planarity at the diffusion bond interface.

It has been determined that time-of-flight imaging can determine if a diffusion bond has a planar ground boundary array. This information can be displayed in graphical or statistical form using a histogram. The information can be displayed two-dimensionally or three-dimensionally as an image of cross sectional area representing the locations in the volume being evaluated and time-of-flight as a color or gray-scale; a region of uniform color or gray. A large areal amount of the display at a given color or level of gray would indicates the presence of a planar array within the volume capable of reflecting sound. Alternatively, the information can be displayed as statistical graph plotting time-of-flight interval versus fraction of total signal received; a sharp peak on this statistical graph would indicate presence of a planar array within the volume capable of reflecting sound.

Time-of-flight characterization can be contrasted to more conventional ultrasonic C-scan imaging which records the amplitude of the reflected sound pulse from all features in the volume, and typically displays the information as an image of cross sectional area at the volume being evaluated and amplitude of reflected signals as a color or gray-scale; a region of uniform color or gray, or a large areal amount of the display at a given color or level of gray would indicate presence of features within the volume which reflect to the same degree. Large differences in reflecting ability ("reflectance") are required to distinguish a feature from the surrounding parent material. Examples include voids, pores and cracks. In the absence of the high reflector features, C-scan imaging is unable to distinguish any undesirable characteristics of the bond line like a planar array of grain boundaries from a diffusion bond, since a planar grain boundary array will consist of individual grain boundaries of random reflectances. Additionally, within the insonified volume there could be grain boundaries of higher reflectance than those on the planar array, and those former reflecting features will be those dominating the C-scan.

Figures 3A, 3B, 3C:
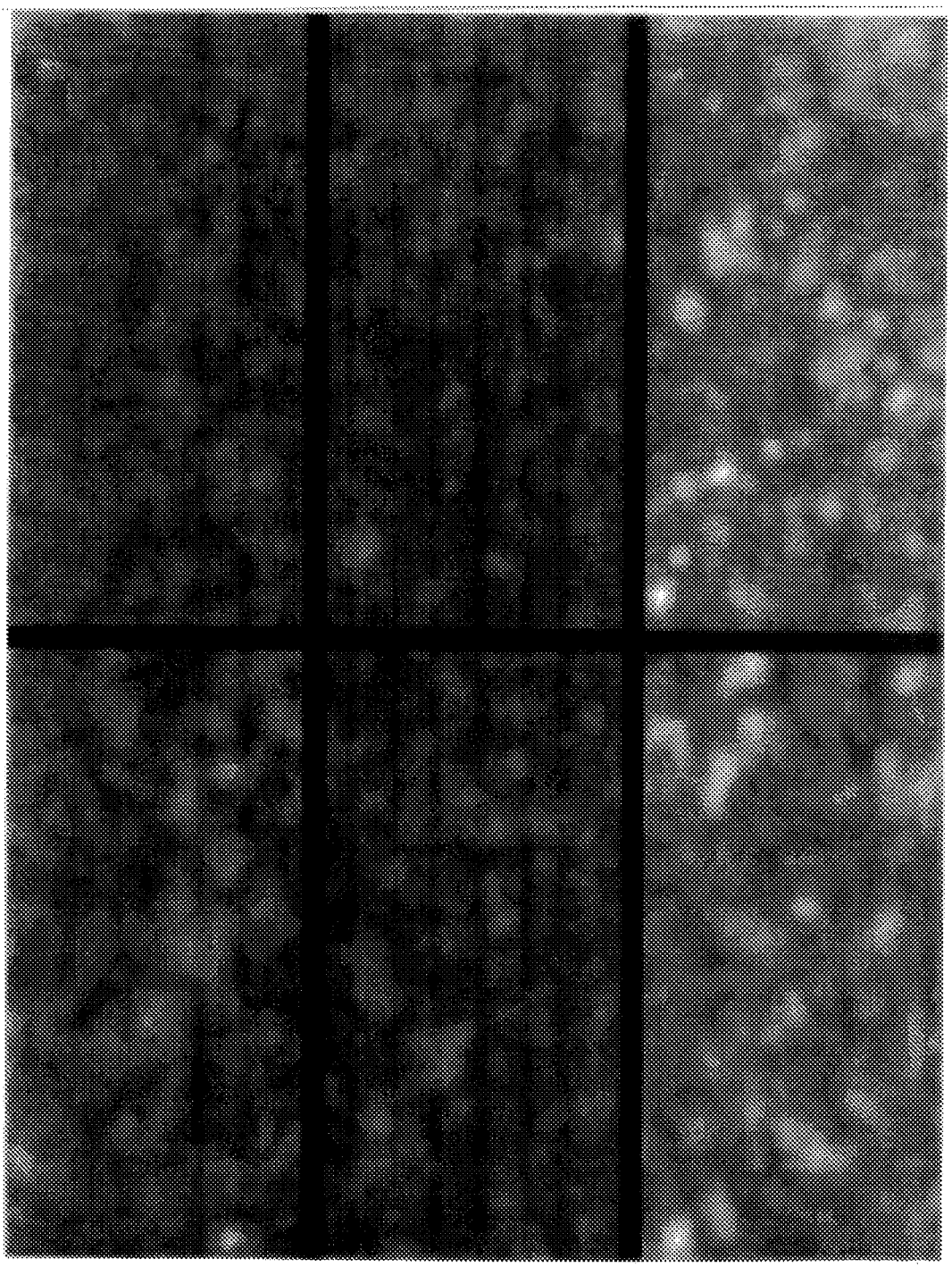
FIGS. 3A–C show C-scan images of the alloy blocks of FIGS. 2A–C, respectively, viewed within the alloy matrix.
Figures 4A, 4B, 4C:
FIGS. 4A–C show C-scan images of the alloy blocks of FIGS. 2A–C, respectively, viewed within the region of the diffusion bond.
Figure 5A:
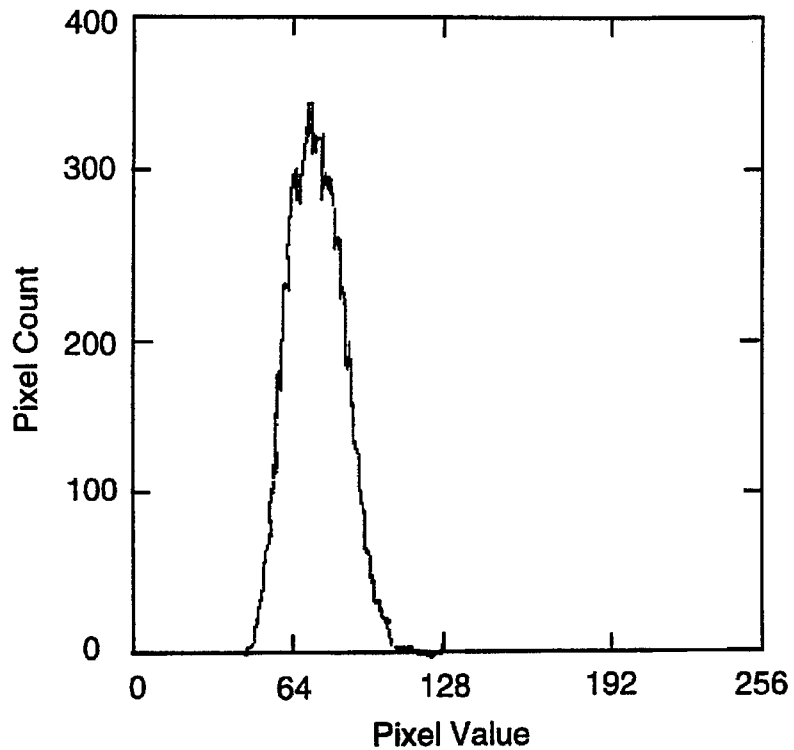
FIGS. 5A–C show C-scan histograms corresponding to the integration of the time of flight information of the C-scan images of FIGS. 3A–C, respectively.
Figure 6A:
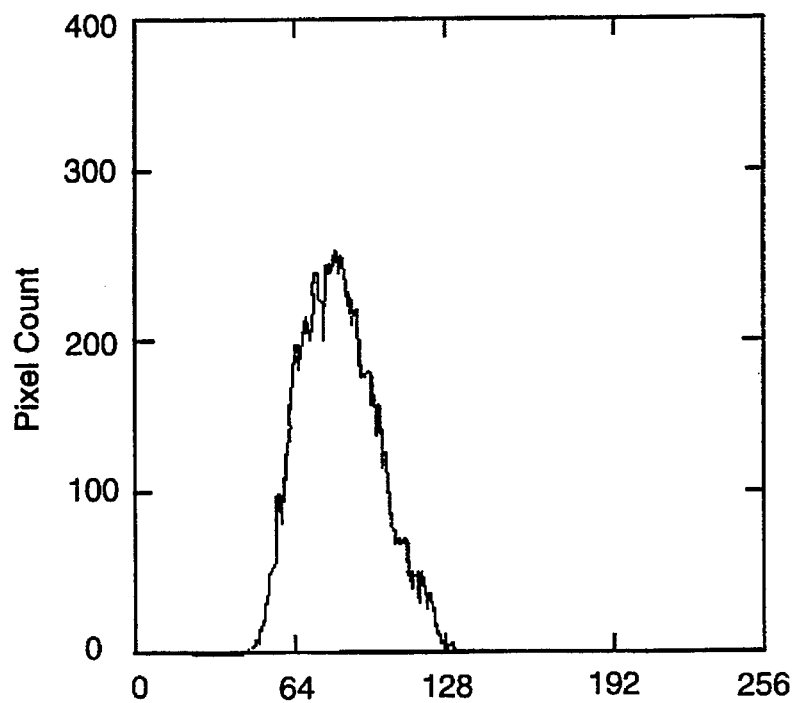
FIGS. 6A–C show C-scan histograms corresponding to the integration of the time of flight information of the C-scan images of FIGS. 4A–C, respectively.
Figure 5B:
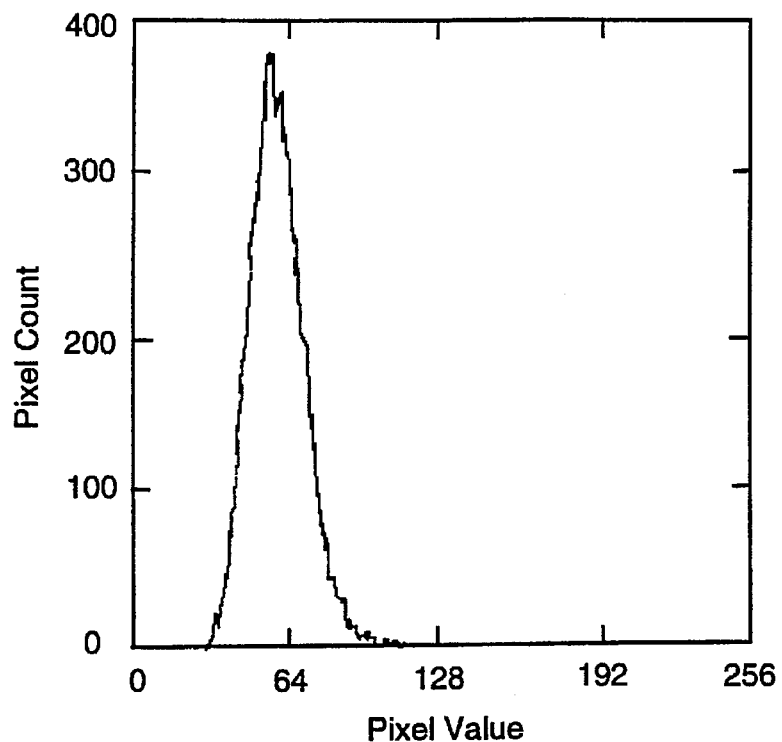
Figure 6B:
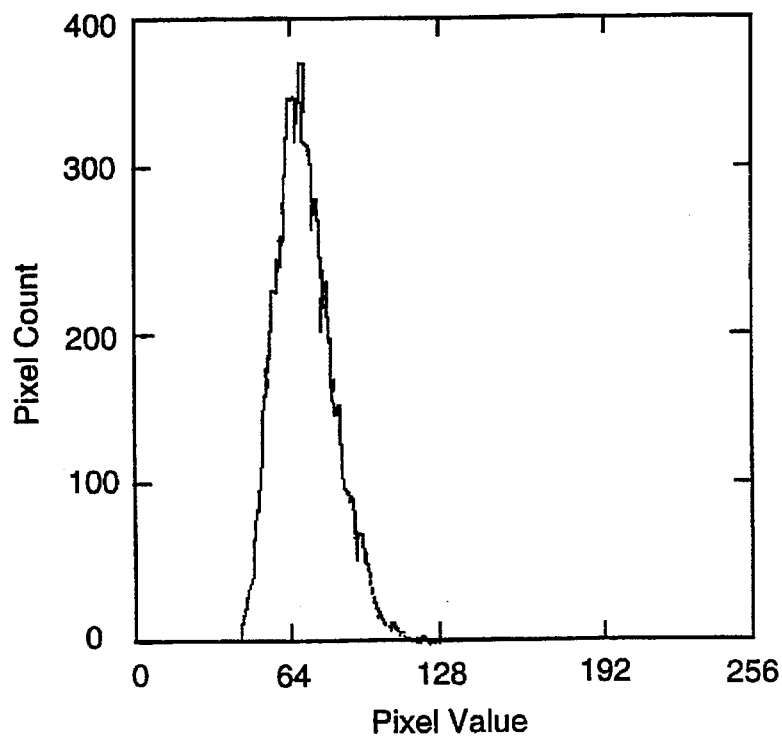
Figure 5C:
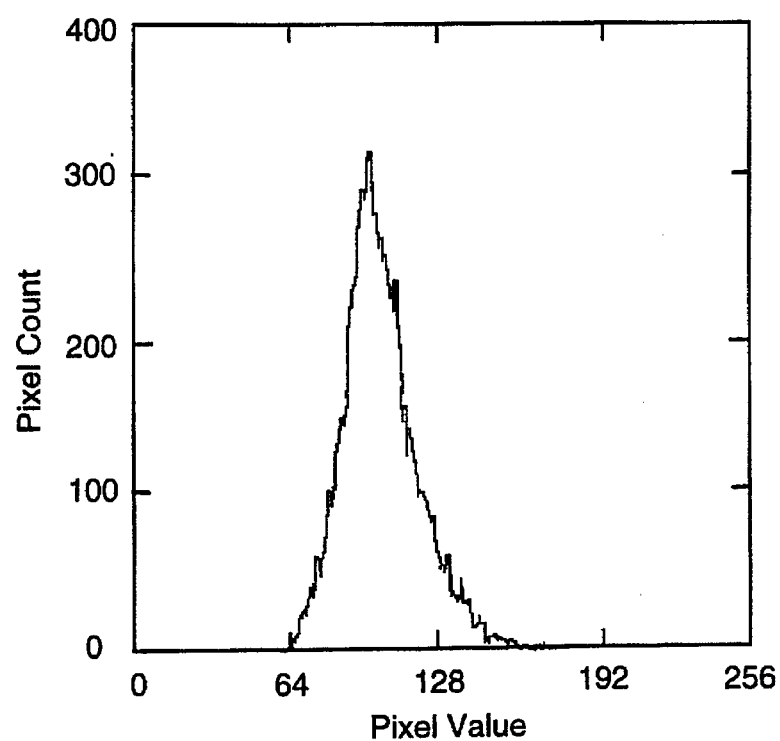
Figure 6C:
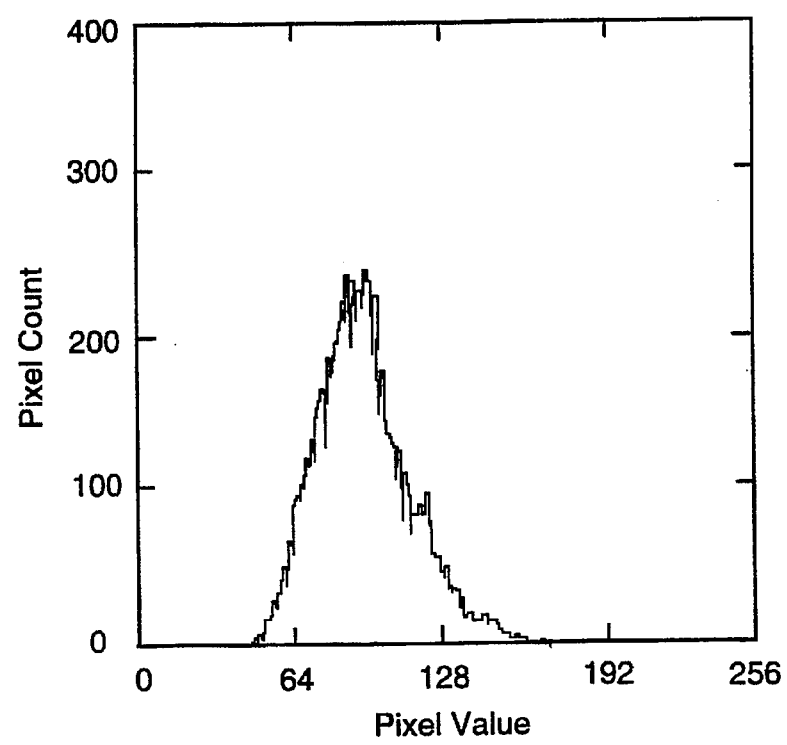

FIGS. 3A–C show the C-scan images of the Samples 17H1, 17H2 and 17H3 (FIGS. 2A–C), respectively, within the alloy matrix. FIGS. 4A–C show the C-scan images of the Samples 17H1, 17H2 and 17H3 (FIGS. 2A–C), respectively, within the diffusion bond. As may be seen, these images do not reveal any significant differences between the two locations in a given sample, or between different samples. As may also be seen in FIGS. 5A–C and 6A–C, the histograms for the C-scans at these locations also do not reveal any significant differences between the two locations measured in a given Sample, or between different Samples. FIGS. 5A–C show the histograms of the C-scan information collected for Samples 17H1, 17H2 and 17H3 (FIGS. 2A–C), respectively, within the alloy matrix. FIGS. 6A–C show the histograms of the C-scan information collected for Samples 17H1, 17H2 and 17H3 (FIGS. 2A–C), respectively, within the diffusion bond. No appreciable difference in either the images or the histogram can be seen within or between the Samples.

Figures 7A, 7B, 7C, 8A, 8B, 8C:
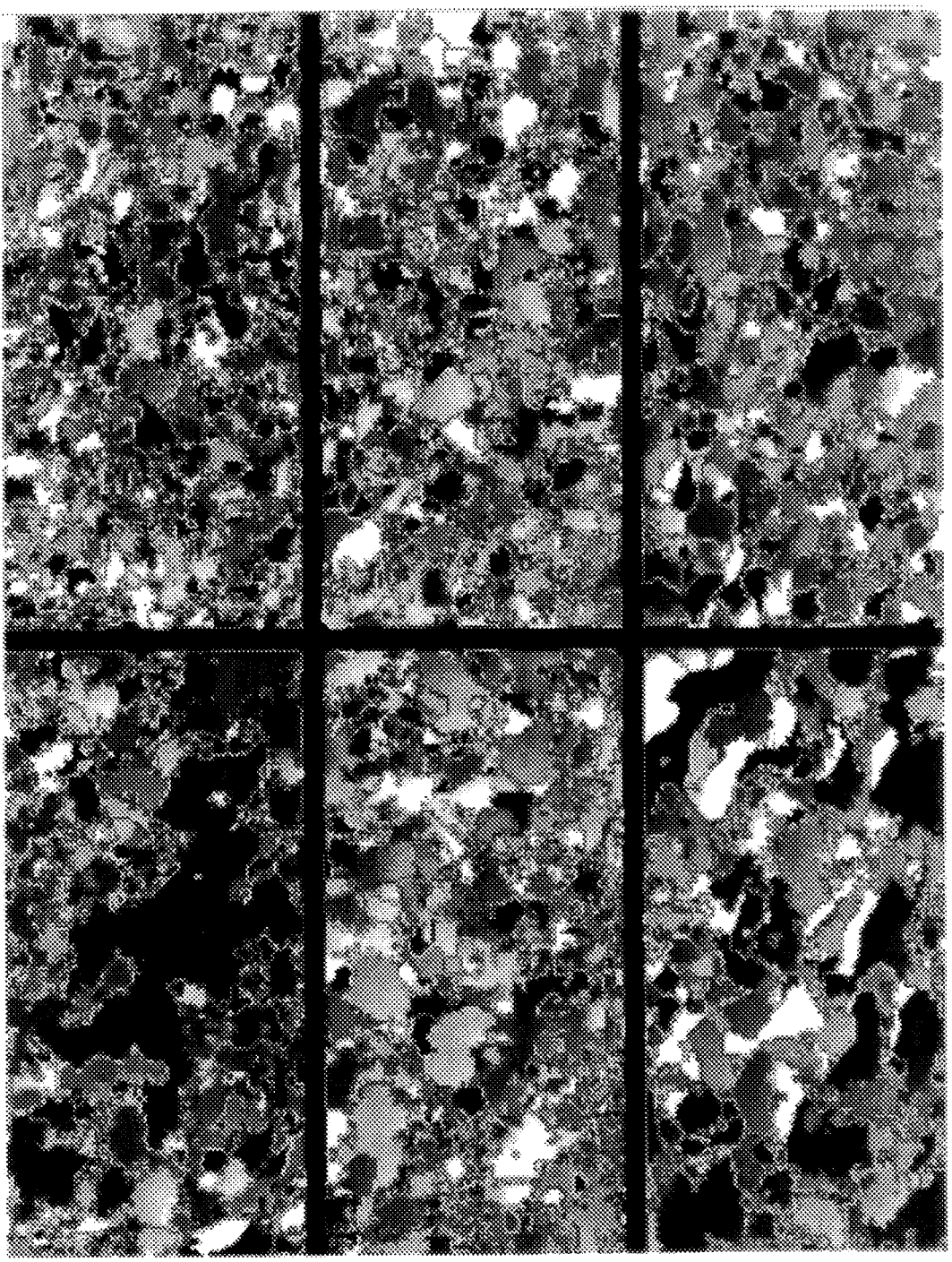
FIGS. 7A–C show time of flight images of the alloy blocks of FIGS. 2A–C, respectively, viewed within the alloy matrix.
FIGS. 8A–C show time of flight images of the alloy blocks of FIGS. 2A–C, respectively, viewed within the region of the diffusion bond.
Figure 9A:
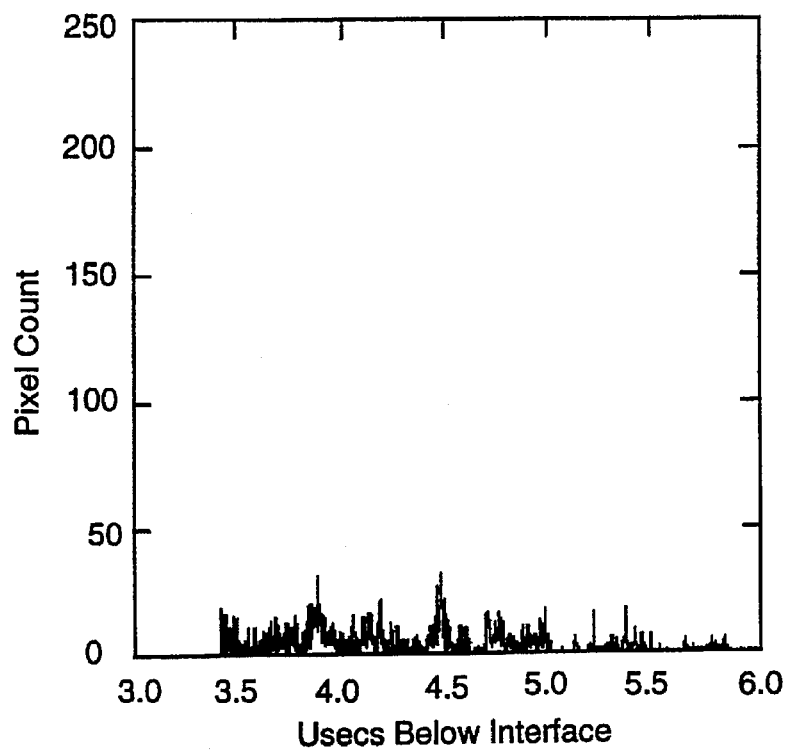
FIGS. 9A–C show time of flight histograms corresponding to the integration of the time of flight information of the time of flight images of FIGS. 7A–C, respectively.
Figure 10A:
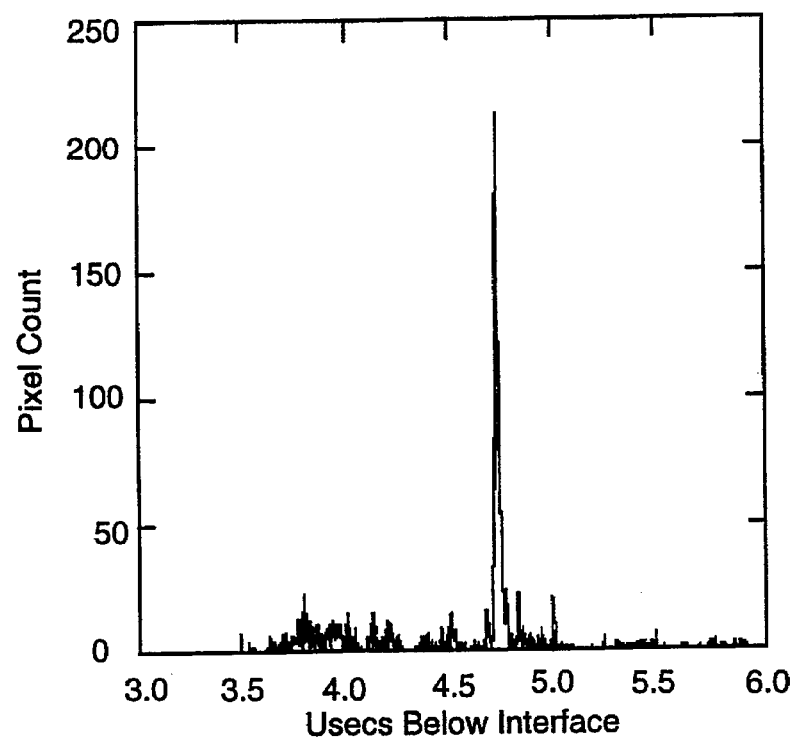
FIGS. 10A–C show time of flight histograms corresponding to the integration of the time of flight information of the time of flight images of FIGS. 8A–C, respectively.
Figure 9B:
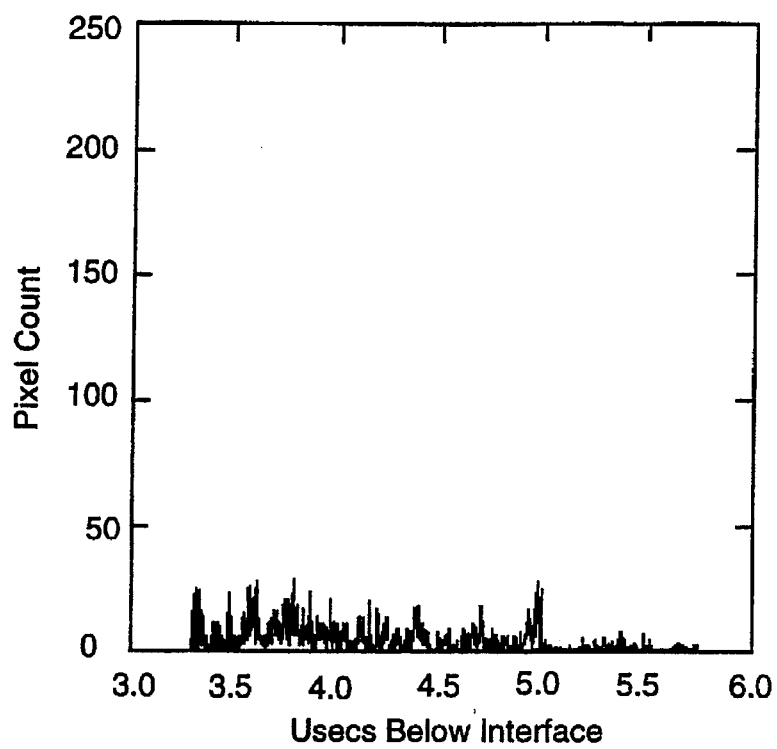
Figure 10B:
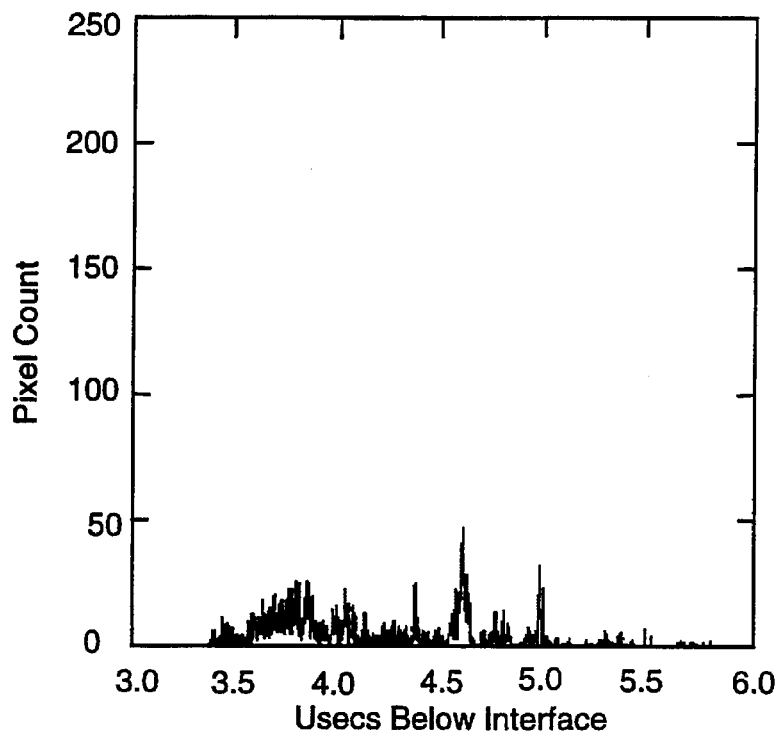
Figure 9C:
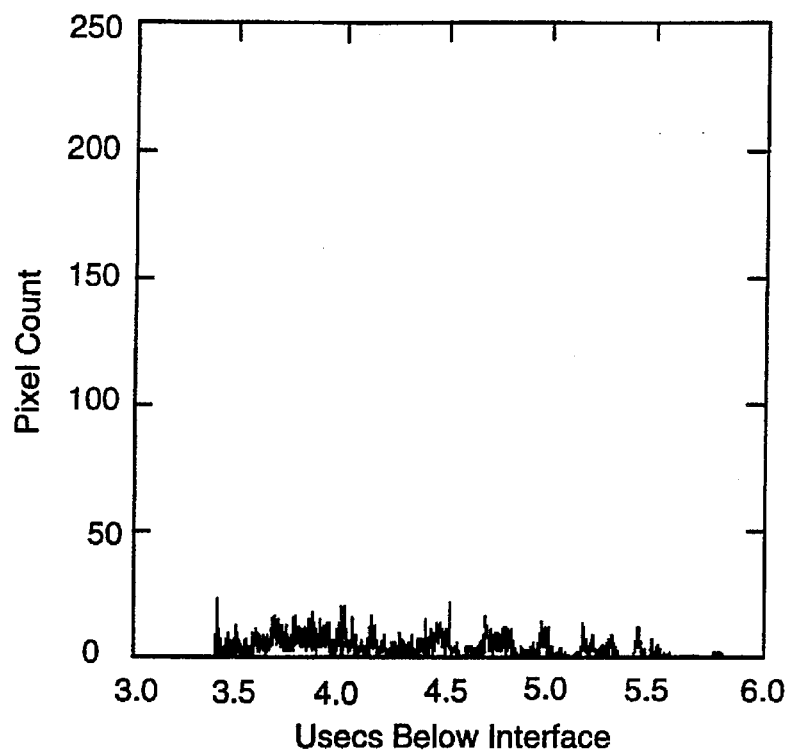
Figure 10C:
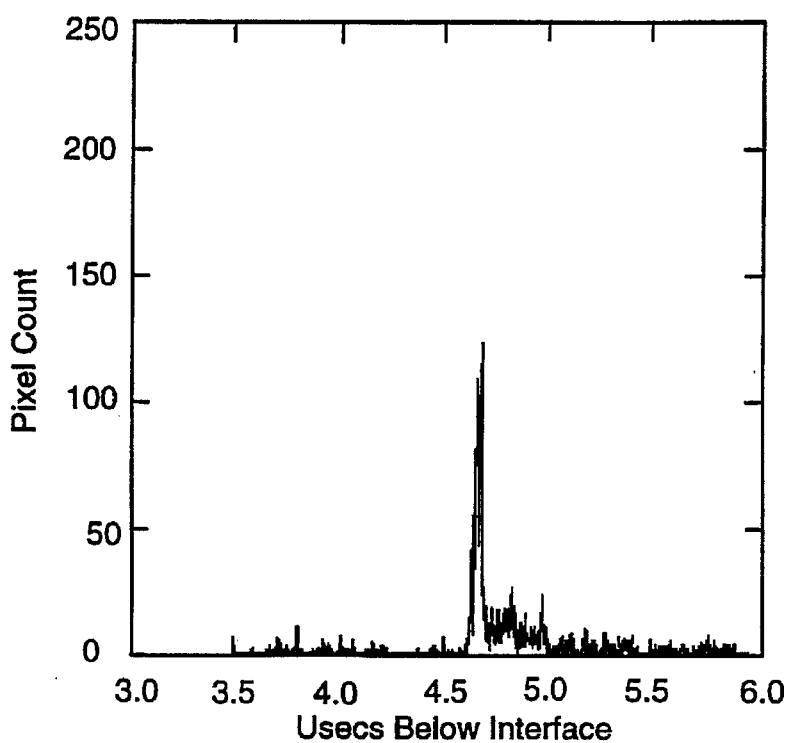

FIGS. 7A–C show two-dimensional time of flight images of the Samples 17H1, 17H2 and 17H3 (FIGS. 2A–C), respectively, within the alloy matrix, where location corresponds to a point in the two-dimensional image, and time of flight ($TOF_M$) is represented by a variation in gray-scale tone. FIGS. 8A–C show the time of flight images of the Samples 17H1, 17H2 and 17H3 (FIGS. 2A–C), respectively, within the diffusion bond. As may be seen, a comparison of FIGS. 7A and 7C with FIGS. 8A and 8C, respectively, does reveal a significant differences between the time of flight information obtained within each of these Samples at the two locations. Samples 8A and 8C (taken at the diffusion bond interface) show large regions with the same, or substantially similar, times of flight, corresponding Samples 17H1 and 17H3 are the Samples which exhibited a planar grain boundary array in the diffusion bond region by metallographic inspection, as described above. The images of FIGS. 7B and 8B, however, are similar to one another, and to FIGS. 7A and 7C (taken in the alloy matrix), and thus do not indicate the presence of a planar grain boundary array in the diffusion bond region of Sample 17H2. Thus, time of flight information may be used to detect certain microstructural features as described herein. This is further confirmed by FIGS. 9A–C and 10A–C. FIGS. 9A–C show the histograms of the time of flight information collected for Samples 17H1, 17H2 and 17H3 (FIGS. 2A–C), respectively, within the alloy matrix. FIGS. 10A–C show the histograms of the time of flight information collected for Samples 17H1, 17H2 and 17H3 (FIGS. 2A–C), respectively, within the diffusion bond. Again, Samples 17H1 and 17H3 (FIGS. 10A and 10C) exhibit a readily observable peak in the integrated time of flight information taken in the diffusion bond region, indicative of a planar grain boundary array, while the information for Sample 17H2 (FIG. 10B) does not exhibit a distinct peak.

Figure 11:
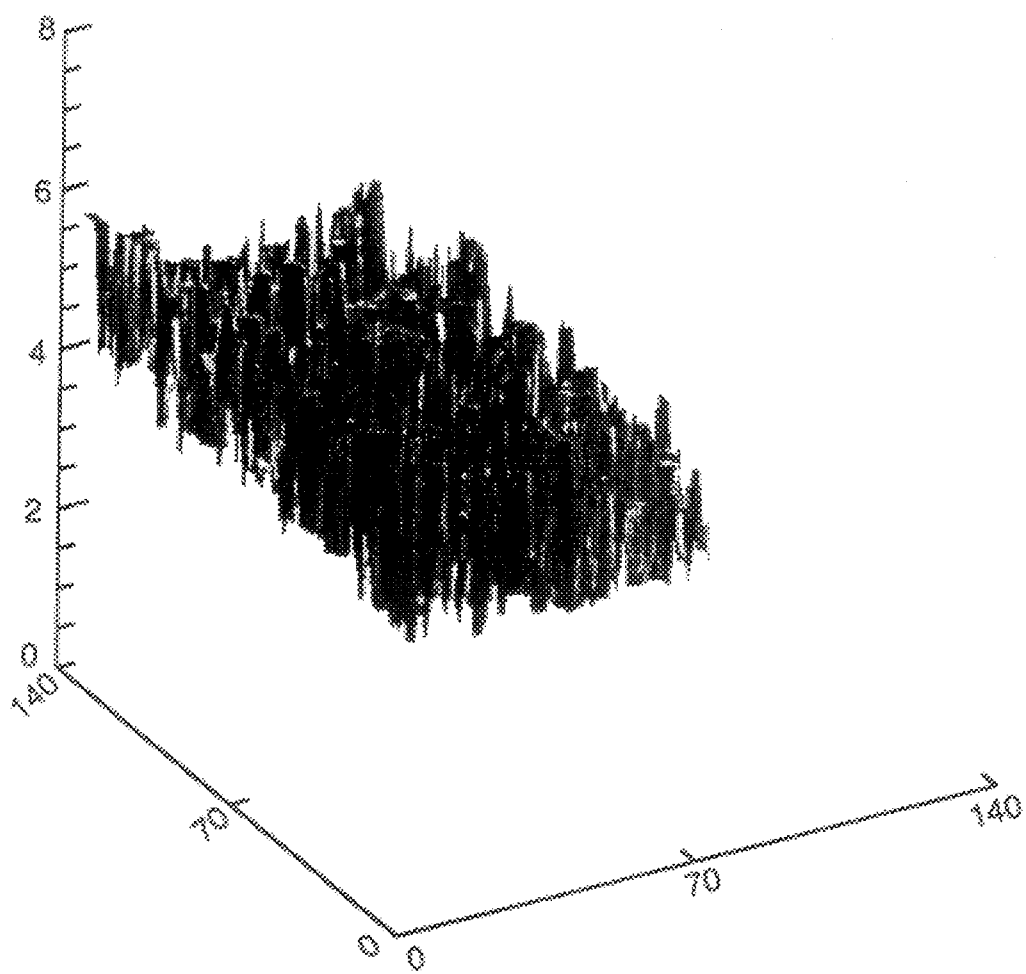
FIG. 11 is a three-dimensional plot of time of flight (z-axis) as a function of location (x-axis and y-axis) for the sample of FIG. 2A at locations within the alloy matrix.
Figure 12:
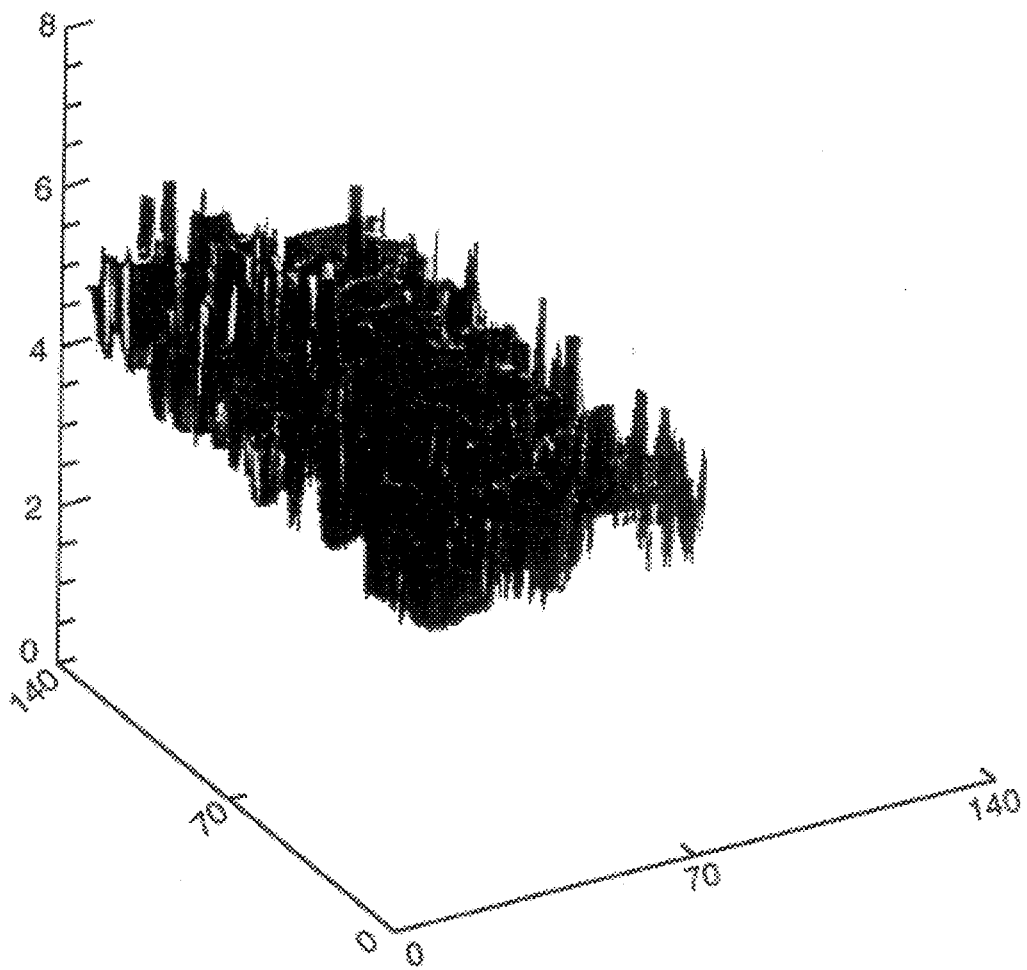
FIG. 12 is a three-dimensional plot of time of flight (z-axis) as a function of location (x-axis and y-axis) for the sample of FIG. 2A at locations within the diffusion bond.
Figure 13:
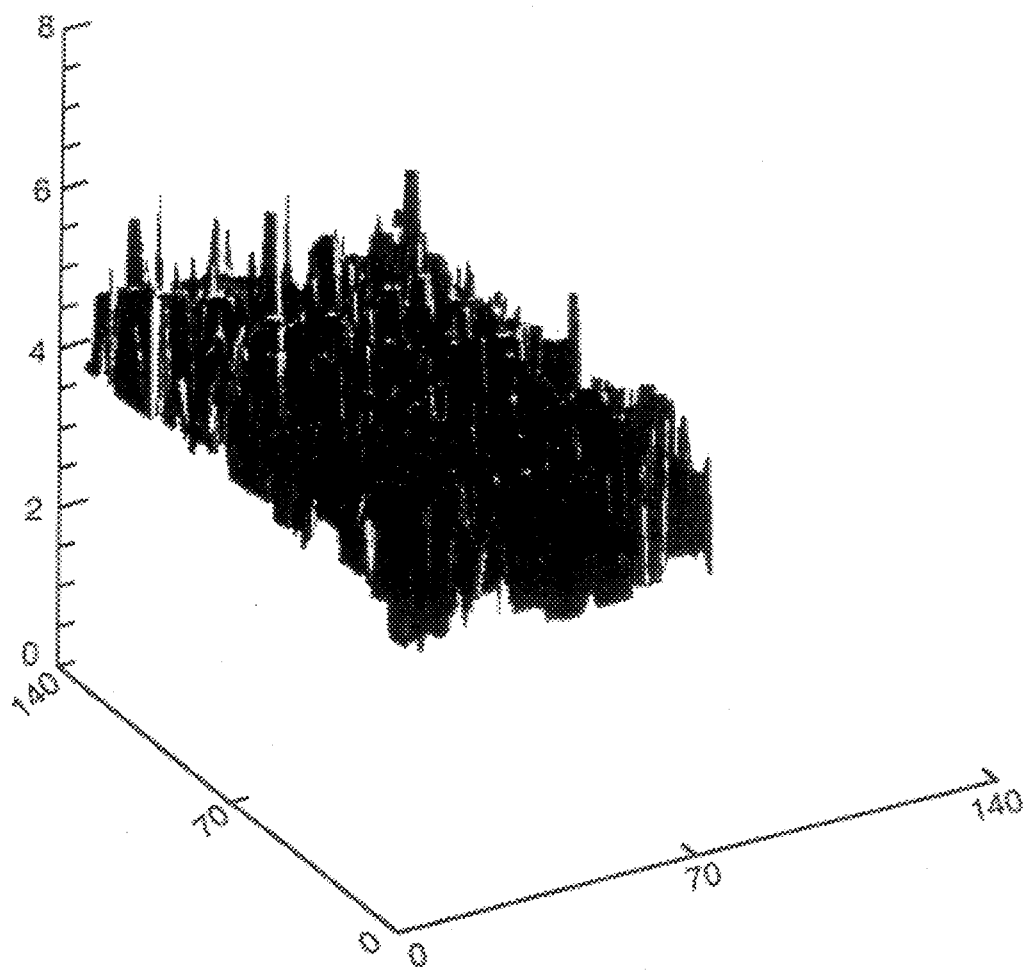
FIG. 13 is a three-dimensional plot of time of flight (z-axis) as a function of location (x-axis and y-axis) for the sample of FIG. 2B at locations within the diffusion bond.

Another three-dimensional representation of the time of flight information described in FIGS. 7A–C, 8A–C, 9A–C, 10A–C is shown in FIGS. 11–13. Generally speaking, FIGS. 11–13 shows the location information (x-axis and y-axis) as a function of the time of flight ($TOF_M$) at that location (z-axis). FIG. 11 shows the $TOF_M$ information obtained from Sample 17H1 in the alloy matrix, while FIG. 12 shows the $TOF_M$ information obtained from Sample 17H1 in the region of the diffusion bond. FIG. 13 shows the $TOF_M$ information obtained from Sample 17H2 in the region of the diffusion bond. These results are of course consistent with those observed using the other means of comparison for this information, but are included to demonstrate the flexibility of the comparison means available using the method of this invention.

The foregoing embodiments have been disclosed for the purpose of illustration of the present invention, and are not intended to be exhaustive of the potential variations thereof. Variations and modifications of the disclosed embodiments will be readily apparent those skilled in the art. All such variations and modifications are intended to be encompassed by the claims set forth hereinafter.

What is claimed is:

1. A method of detecting and evaluating microstructural features comprising regions of grain orientation or crystallographic texture, grain boundary orientation or grain size differential within a volume of a material having a microstructure comprising a plurality of randomly oriented grains defining a randomly oriented network of grain boundaries, comprising the steps of:

insonification of a plurality of locations within the volume of the material by using a transducing means to send an ultrasonic pulse through each location, whereby the ultrasonic pulse produces at each location a plurality of reflections characteristic of the microstructure of the material at that location, each reflection having a characteristic amplitude and time of flight;

detection of the amplitude and the time of flight for each of the plurality of reflections at each location;

identification of a time of flight ($TOF_M$) value of the reflection at each location having the largest amplitude;

storing information comprising the $TOF_M$ value at each location and the associated location in an information storage means; and comparing the value of $TOF_M$ at one location with the values of $TOF_M$ at a plurality of other locations for the purpose of determining whether a region of adjacent locations exist having the same $TOF_M$, whereby a region of adjacent locations having the same values of $TOF_M$ are indicative of grain orientation or grain boundary orientation within the material.

2. The method of claim 1, wherein the transducing means is a focused beam immersion ultrasonic transducer or focused contact ultrasonic transducer.

3. The method of claim 1, wherein the transducing means comprises a plurality of ultrasonic transducers.

4. The method of claim 1, wherein the step of detection is accomplished using the transducing means.

5. The method of claim 1, wherein the step of comparing comprises converting the information into a histogram wherein the time of flight or a linear distance within the material is represented along one axis and the number of locations having a $TOF_M$ at a particular time of flight or a linear distance is represented along the other axis.

6. The method of claim 1, wherein the step of comparing comprises converting the information into a two-dimensional representation wherein the plurality of locations that have been insonified are represented by a corresponding plurality of points and the associated time of flight or a linear distance within the material at each of the plurality of points is represented by a symbol associated with that time of flight or distance, such that each different time of flight or distance has a distinct symbol.

7. The method of claim 6, wherein the symbol is a color or gray-scale shade.

8. The method of claim 1, wherein the step of comparing comprises converting the information into a three-dimensional plot wherein the plurality of locations that have been insonified are represented by a corresponding plurality of points (x,y) measured along an x-axis and a y-axis, and the associated time of flight or a linear distance within the material at each of the plurality of points is represented by a point (z) measured along a z-axis.

9. The method of claim 1, further comprising the step of using the detected amplitudes from the reflected ultrasonic pulses to develop a C-scan comparison of these amplitudes, wherein C-scan images available from such C-scan comparisons may be used in conjunction with results from the step of comparing $TOF_M$ information.

10. A method of evaluating an article formed by bonding together a plurality of materials, each material having a microstructure comprising a plurality of randomly oriented grains defining a randomly oriented network of grain boundaries, and containing an internal interface where the materials are bonded to one another, comprising the steps of:

insonification of a plurality of locations within the article, including locations that comprise the internal interface, by using a transducing means to send an ultrasonic pulse through each location, whereby the ultrasonic pulse produces at each location a plurality of reflections characteristic of the microstructure of the materials at that location, each reflection having a characteristic amplitude and time of flight;

detection of the amplitude and the time of flight for each of the plurality of reflections at each location;

identification of a time of flight ($TOF_M$) value of the reflection at each location having the largest amplitude;

storing information comprising the $TOF_M$ value at each location and the associated location in an information storage means; and comparing the value of $TOF_M$ at one location with the values of $TOF_M$ at a plurality of other locations for the purpose of determining whether a region of adjacent locations exist having the same $TOF_M$, whereby a region of adjacent locations at the internal interface having the same values of $TOF_M$ are indicative of incomplete bonding between the materials.

11. The method of claim 10, wherein the materials are bonded by diffusion bonding, roll bonding, hot pressing, HIPing or welding.

12. The method of claim 10, wherein the transducing means is a focused beam immersion ultrasonic transducer or focused contact ultrasonic transducer.

13. The method of claim 10, wherein the transducing means comprises a plurality of ultrasonic transducers.

14. The method of claim 10, wherein the step of detection is accomplished using the transducing means.

15. The method of claim 10, wherein the step of comparing comprises converting the information into a histogram wherein the time of flight or a linear distance within the materials is represented along one axis and the number of locations having a $TOF_M$ at a particular time of flight or a linear distance is represented along the other axis.

16. The method of claim 10, wherein the step of comparing comprises converting the information into a two-dimensional representation wherein the plurality of locations that have been insonified are represented by a corresponding plurality of points and the associated time of flight or a linear distance within the materials at each of the plurality of points is represented by a symbol associated with that time of flight or distance, such that each different time of flight or distance has a distinct symbol.

17. The method of claim 16, wherein the symbol is a color or gray-scale shade.

18. The method of claim 10, wherein the step of comparing comprises converting the information into a three-dimensional plot wherein the plurality of locations that have been insonified are represented by a corresponding plurality of points (x,y) measured along an x-axis and a y-axis, and the associated time of flight or a linear distance within the materials at each of the plurality of points is represented by a point (z) measured along a z-axis.

19. The method of claim 10, further comprising the step of using the detected amplitudes from the reflected ultrasonic pulses to develop a C-scan comparison of these amplitudes, wherein C-scan images and other information available from such C-scan comparisons may be used in conjunction with results from the step of comparing $TOF_M$ information.

* * * * *